(12) United States Patent
Czipott et al.

(10) Patent No.: US 7,154,266 B2
(45) Date of Patent: *Dec. 26, 2006

(54) SCREENING METHOD AND APPARATUS

(75) Inventors: Peter V. Czipott, San Diego, CA (US); Sankaran Kumar, San Marcos, CA (US); Lowell J. Burnett, El Cajon, CA (US); Stephen Wolff, San Diego, CA (US); Richard J. McClure, San Diego, CA (US)

(73) Assignee: Quantum Magnetics, Inc., San Diego, CA (US)

( * ) Notice: Subject to any disclaimer, the term of this patent is extended or adjusted under 35 U.S.C. 154(b) by 151 days.

This patent is subject to a terminal disclaimer.

(21) Appl. No.: 10/757,029

(22) Filed: Jan. 13, 2004

(65) Prior Publication Data

US 2004/0189293 A1    Sep. 30, 2004

Related U.S. Application Data

(63) Continuation-in-part of application No. 10/723,457, filed on Nov. 25, 2003, now Pat. No. 6,956,369, which is a continuation-in-part of application No. 10/703,147, filed on Nov. 5, 2003, which is a continuation of application No. 10/681,033, filed on Oct. 7, 2003, application No. 10/723,457, which is a continuation-in-part of application No. 10/681,033, filed on Oct. 7, 2003.

(60) Provisional application No. 60/440,697, filed on Jan. 17, 2003, provisional application No. 60/489,250, filed on Jul. 22, 2003.

(51) Int. Cl.
*G01R 33/00*    (2006.01)

(52) U.S. Cl. .................. 324/244; 324/228; 324/260

(58) Field of Classification Search ................ 324/244, 324/228, 260
See application file for complete search history.

(56) References Cited

U.S. PATENT DOCUMENTS

| | | | |
|---|---|---|---|
| 3,781,664 A | 12/1973 | Rorden | |
| 3,971,983 A | 7/1976 | Jaquet | |
| 4,060,039 A | 11/1977 | Lagarrigue | |
| 4,068,164 A | 1/1978 | Schwartz et al. | |
| 4,135,183 A * | 1/1979 | Heltemes ................. | 340/572.7 |
| 4,193,024 A | 3/1980 | Hoult et al. | |

(Continued)

FOREIGN PATENT DOCUMENTS

WO    WO 03/091753 A1    11/2003

(Continued)

OTHER PUBLICATIONS

Finn, Edward J., et al., Ferromagnetic Materials in Patients: detection before MR Imaging; Radiology; Jul. 1985; vol. 185; pp. 139-141.

(Continued)

*Primary Examiner*—Bot LeDynh
(74) *Attorney, Agent, or Firm*—Gerald W. Spinks

(57) ABSTRACT

A method and apparatus to screen individuals specifically for paramagnetic or ferromagnetic objects they may be carrying or wearing, before they enter a controlled area. The device comprises a screening portal, including multiple sensor arrays and associated electronics. The device places the sensor arrays in close proximity to a subject's body, including the head and feet if desired, for screening purposes. The portal can have multiple excitation sources oriented to generate a multi-axis excitation field, and multi-axis sensors. The portal can also have an interlock with the door of the controlled area.

33 Claims, 9 Drawing Sheets

U.S. PATENT DOCUMENTS

| | | | |
|---|---|---|---|
| 4,734,643 | A | 3/1988 | Bubenik et al. |
| 4,837,489 | A | 6/1989 | McFee |
| 5,175,419 | A | 12/1992 | Yamashita |
| 5,321,361 | A | 6/1994 | Goodman |
| 5,379,334 | A | 1/1995 | Zimmer et al. |
| 5,397,986 | A * | 3/1995 | Conway et al. ............. 324/243 |
| 5,408,178 | A | 4/1995 | Wikswo, Jr. et al. |
| 5,493,517 | A | 2/1996 | Frazier |
| 5,494,033 | A | 2/1996 | Buchanan et al. |
| 5,494,035 | A | 2/1996 | Leuthold et al. |
| 5,504,428 | A | 4/1996 | Johnson |
| 5,610,518 | A | 3/1997 | Chamberlain, IV |
| 5,689,184 | A | 11/1997 | Jeffers et al. |
| 5,705,924 | A | 1/1998 | Jeffers |
| 5,735,278 | A | 4/1998 | Hoult et al. |
| 5,757,183 | A | 5/1998 | Smith et al. |
| 5,842,986 | A | 12/1998 | Avrin |
| 6,064,208 | A | 5/2000 | Steckner |
| 6,087,832 | A | 7/2000 | Doty |
| 6,133,829 | A | 10/2000 | Johnstone et al. |
| 6,150,810 | A | 11/2000 | Roybal |
| 6,208,884 | B1 | 3/2001 | Kumar et al. |
| 6,362,739 | B1 | 3/2002 | Burton |
| 6,384,603 | B1 | 5/2002 | Hoult et al. |
| 6,418,335 | B1 | 7/2002 | Avrin et al. |
| 6,496,713 | B1 | 12/2002 | Avrin et al. |
| 6,541,966 | B1 | 4/2003 | Keene |
| 6,670,809 | B1 * | 12/2003 | Edelstein et al. ........... 324/244 |
| 2002/0115925 | A1 | 8/2002 | Avrin et al. |
| 2002/0151779 | A1 | 10/2002 | Avrin et al. |
| 2003/0083588 | A1 | 5/2003 | McClure et al. |
| 2003/0171669 | A1 | 9/2003 | Kopp |
| 2003/0216632 | A1 | 11/2003 | McClure et al. |
| 2004/0135687 | A1 | 7/2004 | Keene |

FOREIGN PATENT DOCUMENTS

| | | |
|---|---|---|
| WO | WO 03091753 | 11/2003 |
| WO | WO 04/044620 A1 | 5/2004 |

OTHER PUBLICATIONS

Institute for Biodiagnostics; MRI Safety: Detection of Ferromagnetic Objects; Date unknown; 8 pages; National Research Council Canada.

Kopp Development; Ferralert Brochure; Date Unknown; 2 pages; Kopp Development; Jensen Beach, FL.

Kotter, David K., et al..; Abstract: Detection and Classification of Concealed Weapons Using a Magnetometer-based Portal; NASA ADS Instrumentation Abstract Service; Aug. 2002; 1 page; The International Society for Optical Engineering.

Melodi Metal Locator Gets Straight to the Point; Medica 2002; Nov. 2002; 4 pages; Düsseldorf, Germany.

Metal Detector Finds Lost Coins in Kids; CNN.com/TECHNOLOGY; Jan. 29, 2003; 2 pages; Cable News Network.

Quantum Magnetics; i-Portal 100 Advanced Weapons Detection Portal Brochures; Date unknown; 8 pages.

Mednovus/Quantum Magnetics; Safescan Portal 9000 Series Brochure; 1 page.

ETS-Lindgren; *Ferrogaurd Unveiled at RSNA 2003*; The Quiet Zone; Jan. 2004; p. 11.

ETS-Lindgren Website; *Ferromagnetic Detection System*; May 29, 2004; 2 pages.

CMP United Business Media Website; Metal detector gaurds the door to screen ferromagnetic objects; Diagnostic Imaging SCAN; Jan. 28, 2004; 2 pages.

* cited by examiner

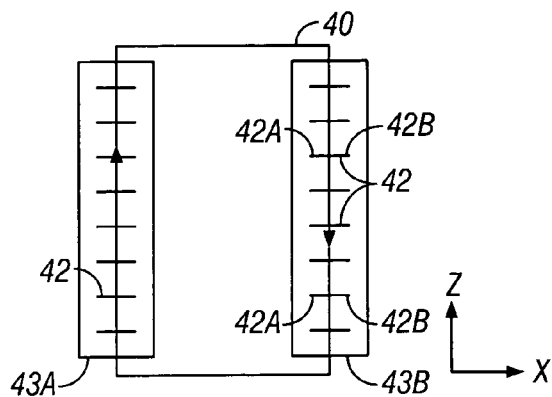
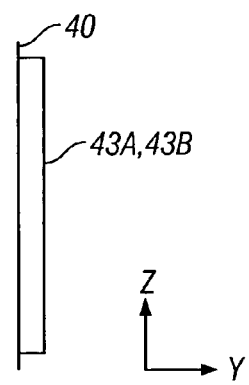
FIG. 8  FIG. 9
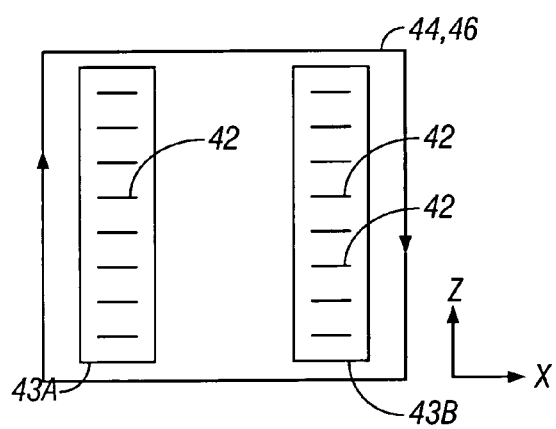
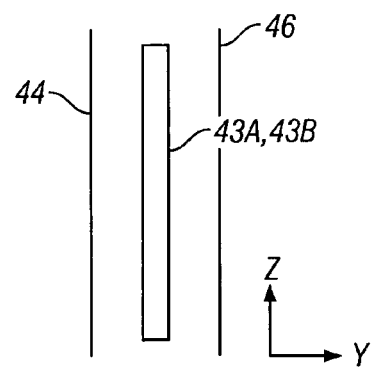
FIG. 10  FIG. 11

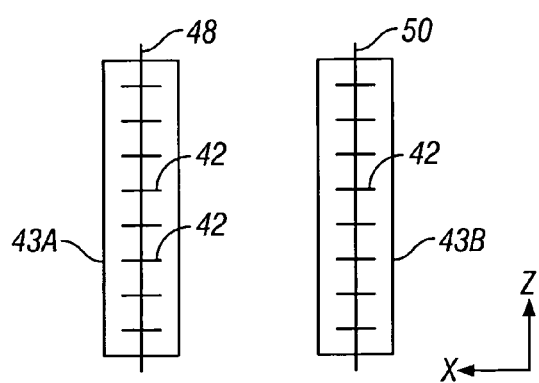
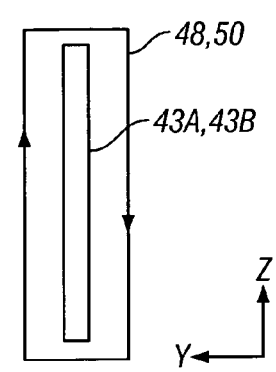
FIG. 12                    FIG. 13

SCREENING METHOD AND APPARATUS

CROSS REFERENCE TO RELATED APPLICATIONS

This is a continuation-in-part application of U.S. app. Ser. No. 10/723,457, filed Nov. 25, 2003, now U.S. Pat. No. 6,956,369 for "Screening Method and Apparatus", which is a continuation-in-part application of U.S. app. Ser. No. 10/681,033, filed Oct. 7, 2003, for "Magnetic Resonance Imaging Screening Method and Apparatus", and a continuation-in-part application of U.S. app. Ser. No. 10/703,147, filed Nov. 5, 2003, for "Security Screening Method and Apparatus", which is a continuation application of U.S. app. Ser. No. 10/681,033, filed Oct. 7, 2003, for "Magnetic Resonance Imaging Screening Method and Apparatus". This application also relies upon U.S. Provisional Pat. App. No. 60/440,697, filed Jan. 17, 2003, for "Method and Apparatus to Use Magnetic Entryway Detectors for Pre-MRI Screening".

STATEMENT REGARDING FEDERALLY SPONSORED RESEARCH OR DEVELOPMENT

Not Applicable

BACKGROUND OF THE INVENTION

1. Field of the Invention

The present invention is in the field of methods and apparatus used to prevent the presence of paramagnetic or ferromagnetic objects in a controlled area.

2. Background Art

It can be desirable to exclude paramagnetic and ferromagnetic objects from a controlled area. For instance, paramagnetic and ferromagnetic objects are highly unsafe near MRI systems, because the strong magnetic gradients caused by MRI magnets exert a strong force on such objects, potentially turning them into dangerous missiles. Several accidents, some fatal, are known to have occurred as the result of someone inadvertently carrying such an object into the MRI room. Current MRI safety practices rely on signage and training to prevent people from taking such objects into the MRI chamber. Paramagnetic and ferromagnetic objects which can be weapons may also be unsafe in other controlled areas, such as schools.

Use of known conventional metal detectors, whether portals or wands, would not be efficient for the purpose of pre-MRI screening. Further, the fact that pistols usually have a ferromagnetic barrel makes a ferromagnetic detector valuable in the school environment and in other security environments, while eliminating the aggravation of detecting non-ferromagnetic metallic objects, which are less likely to be offensive, and which probably do not carry the risk of a hand-gun. Conventional systems generate an audio-band oscillating or pulsed magnetic field with which they illuminate the subject. The time-varying field induces electrical eddy currents in metallic objects. It is these eddy currents which are detected by the system, to reveal the presence of the metallic objects.

BRIEF SUMMARY OF THE INVENTION

The present invention provides an apparatus and a method for scanning a subject for the presence of an object which is either permanently magnetic or susceptible to being magnetized by an external field. The sensors in this scanning apparatus can be mounted on a portal type frame. The portal arrangement of the scanner arranges the sensors suitably for positioning every sensor in proximity to the body of a subject, as the subject passes through the portal.

The sensors can detect the magnetic field of the object, whether the object is a permanent magnet or merely susceptible to magnetization. Where an external field induces a magnetic field in the object, the external field may be the Earth's magnetic field, or it may be generated by another source, such as a nearby MRI apparatus or a dedicated source such as one mounted on the frame of the apparatus.

The novel features of this invention, as well as the invention itself, will be best understood from the attached drawings, taken along with the following description, in which similar reference characters refer to similar parts, and in which:

BRIEF DESCRIPTION OF THE SEVERAL VIEWS OF THE DRAWINGS

FIGS. 8 and 9 show a first embodiment of the excitation coil configuration relative to the portal structure;

FIGS. 10 and 11 show a second embodiment of the excitation coil configuration relative to the portal structure;

FIGS. 12 and 13 show a third embodiment of the excitation coil configuration relative to the portal structure;

DETAILED DESCRIPTION OF THE INVENTION

The present invention, which applies to both permanently magnetic objects called "hard" ferromagnets and non-permanent magnetically susceptible objects called "soft" ferromagnets, can use magnetometers with good sensitivity at frequencies all the way, or nearly, to DC, i.e., zero frequency. This allows several modes of use:

(1) As a completely passive system, the present invention detects ferromagnetic objects using their permanent magnetization, in the case of "hard" ferromagnets, or the magnetization induced by the Earth's magnetic field, in the case of "soft" ferromagnets.

(2) As a DC magnetic susceptometer, the present invention applies a static DC magnetic field, allowing control and usually enhancement of the magnetization of soft ferromagnets, thus enhancing their detectability.

(3) As an AC magnetic susceptometer, the present invention applies an oscillating AC magnetic field, but at very low frequencies compared to conventional detectors, allowing enhancement of their magnetization. The purpose of AC illumination is to move the signal from DC to a region of lower noise at finite frequency. The AC frequency is preferably chosen to avoid inducing the electrical eddy currents detected by other systems, to suppress the response from non-ferromagnetic metal objects, and thus maintaining the discrimination capability.

The sensors are arranged in such a way that the entire sensor array can be placed in proximity to the body of a subject.

A passive magnetic embodiment of the portal used in one embodiment of the present invention can be similar in some respects to the SecureScan 2000™ weapons detection portal which is manufactured by Quantum Magnetics, Inc., and marketed by Milestone Technology, Inc., or the i-Portal™ weapons detection portal which is marketed by Quantum Magnetics, Inc.

The portal includes two panels of sensors on the sides of the entryway. An array of magnetometers inside each panel enables detection, characterization, and localization of ferromagnetic objects from the soles of the feet to the top of the head. The magnetometer array can take a variety of configurations, and it can use a variety of sensor technologies. For example, a set of 16 single-axis magnetic gradiometers can be arranged with 8 in each panel. Other configurations can include arrays of multi-axis gradiometers, or combinations of single-axis and multi-axis gradiometers. One or more magnetic tensor gradiometers may also be used. A magnetoresistive magnetometer, or any other sensor capable of sensing magnetic field changes at or near zero frequency, can be used.

Figure 1:
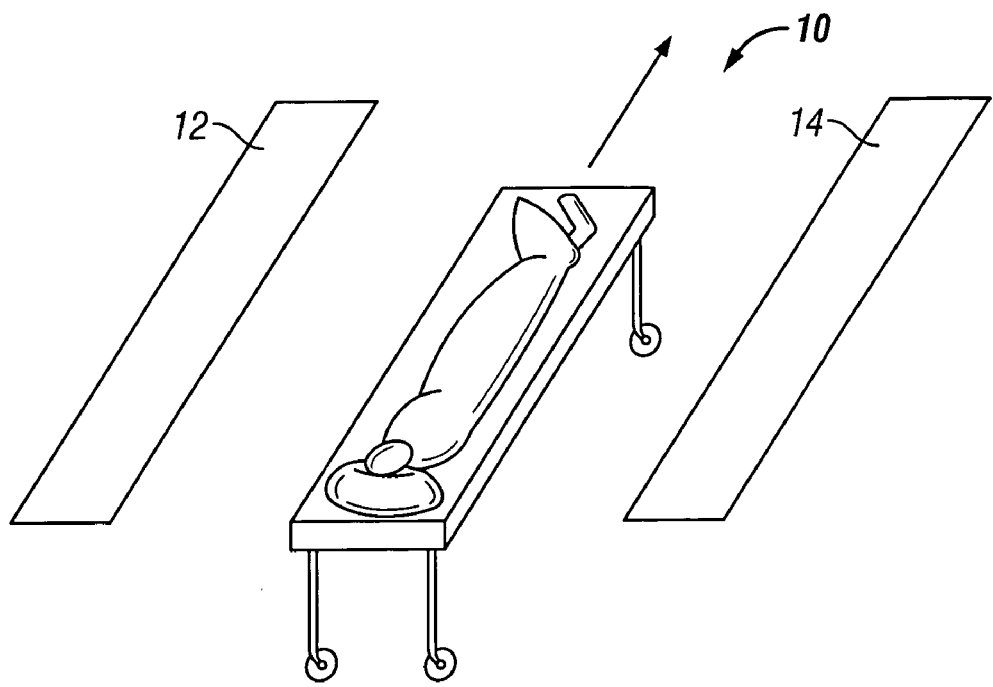
FIG. 1 is a schematic showing the horizontal arrangement of sensor arrays in a first portal type embodiment.

As shown in FIG. 1, in order to scan a patient on a gurney, the portal sensor configuration 10 can be arranged to bring all of the sensors closer to the patient and to effectively scan a patient in the recumbent position. Rather than being arranged vertically, the two sensor panels 12, 14 can be arranged horizontally, parallel to the path of the gurney and on either side, as shown in FIG. 1. This places the sensors in a similar relation to the patient as they would have, in the vertical arrangement, to an ambulatory patient. Also, a single "snapshot" of data covers the entire gurney and patient, as in the ambulatory case. The sensor panels 12, 14 can be permanently arranged horizontally, or they can pivot to this configuration.

Figure 2:
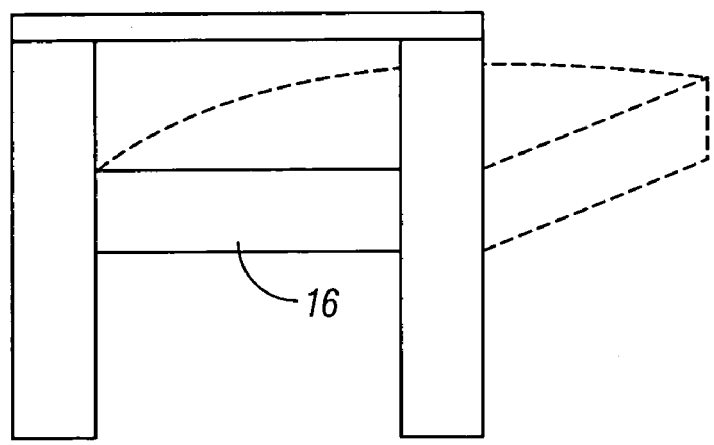
FIG. 2 is a schematic of a second portal embodiment.
Figure 3:
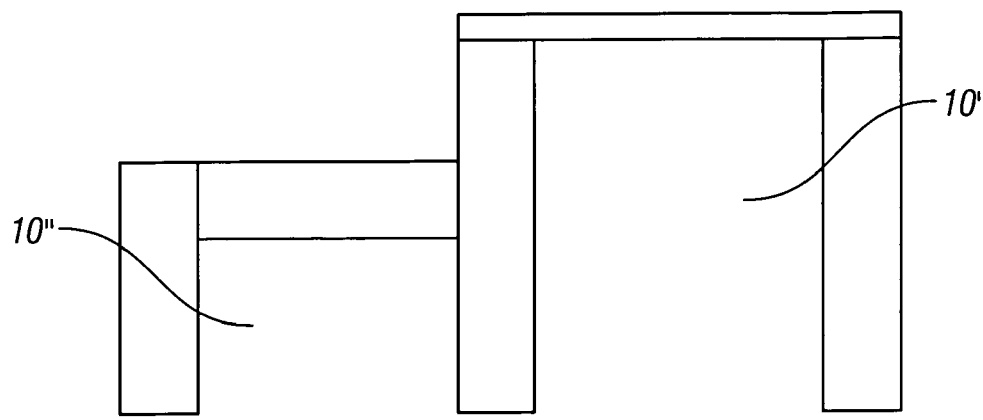
FIG. 3 is a schematic of a third portal embodiment.

Alternatively, in addition to the vertically arranged sensor panels as in the aforementioned known portals, the portal can have a "dutch door" with an additional, horizontal, sensor panel 16 in the upper half of the door, just high enough to clear a patient on a gurney, as shown in FIG. 2. As the patient is wheeled under the upper door, the patient would pass in close proximity to the horizontal sensor panel 16, allowing all of its sensors to scan the patient from head to foot, or vice versa. This gives the best detection and resolution of objects, since more sensors are placed closer to the patient. Then, the attendant would push the dutch door open and walk through the portal, being scanned by the vertically arranged sensor panels. The "dutch door" array 16 can be spring loaded, so that it moves out of the way for an ambulatory subject. A microswitch indicator can tell the software whether the door is engaged, for a recumbent patient, or disengaged, for an ambulatory subject. As a variation, a portal with vertically arranged sensor panels can be situated next to a portal with a horizontally arranged sensor panel, as shown in FIG. 3.

As an alternative to the passive magnetic portal, an AC or DC magnetizing field can be provided by one or more source coils, a DC field can be provided by a permanent magnet array, or a DC field can be provided in the form of the fringing field of a nearby MRI magnet. In any case, a computer is provided to interrogate the sensors and to interpret the magnetic signals, to detect, characterize, and locate ferromagnetic objects. Characterization of the object provides the size and orientation of its magnetic moment, which can be related to the physical size of the object, and to the magnitude of the attractive magnetic force. The analysis software can use various known algorithms, or a neural network can be used. The information gained can be related to a photographic image of the subject, for the purpose of locating the ferromagnetic object on the subject. A light display can be used to indicate the approximate location of the detected object. System diagnosis, monitoring, and signal interpretation can be done via the Internet, if desired.

The use of AC fields enables the use of induction coil sensors, in addition to or instead of magnetometers, like magnetoresistive, fluxgate, and other types. Induction coil sensors are impossible to use in detecting a stationary object with the DC field embodiment, because the induction coil has zero sensitivity at zero frequency. However, when an object to be detected moves through a DC field, this induces an AC magnetic field of very low but finite frequency in the moving object, and this low frequency AC magnetic field can be detected by an induction coil sensor. Using induction coil sensors typically reduces the cost of the product without sacrificing sensitivity, where an AC magnetic field is induced in the object.

An AC system could make use of two or more different excitation directions—operating at two or more different frequencies, to avoid crosstalk—which can improve detection of long, narrow objects, which are precisely the shape that is most dangerous in this situation.

The excitation frequency is chosen to be low enough so that the magnetization (or, equivalently, magnetic susceptibility) response of objects to be detected exceeds their eddy current response. The choice of frequency is expected to be less than 1 kHz, but it can be as high as 3 kHz in some applications.

The excitation current can be driven by any number of standard drive circuits, including either direct drive (controlled voltage source in series with the coil) or a resonant drive (voltage source coupled to the coil via a series capacitance whose value is chosen such that, in combination with the coil's self-inductance, the current is a maximum at a desired resonant frequency given by $1/2\pi(LC)^{1/2}$).

The receiver or sensor coil can be made of two coils, wound in opposite senses and connected in series. They form what is well-known as a gradiometer; a uniform magnetic flux threading both coils produces zero response. The coils are distributed symmetrically relative to the excitation coil such that, in the absence of any target object (which is conductive, magnetic or magnetically permeable) nearby, each senses an identical flux from the excitation which thus cancels out. Higher order gradiometers, also well known, can suppress noise and interference further.

Although the intent is to make the two coils perfectly identical, and to place them in identically symmetric locations, in practice one falls short of the ideal. As a result, any actual embodiment will display a nonzero response to the excitation, even in the absence of a target; this residual common-mode signal is referred to as an "imbalance" signal. Standard electrical circuits can zero out the imbalance signal by adding an appropriately scaled fraction of the reference voltage $V_{ref}$ (a voltage proportional to the excitation current, obtained by measuring across a series monitor resistor) to the output voltage $V_{out}$.

When a target object is near to either coil, it spoils the symmetry and thus induces a finite signal. This signal oscillates at the same frequency as the excitation. Standard demodulation or phase-sensitive detection circuits, using $V_{ref}$ as the phase reference, measure the magnitude of $V_{out}$ in phase with $V_{ref}$ and in quadrature (90 degrees out of phase) with $V_{ref}$. At an appropriately chosen low frequency, the response will be dominated by the susceptibility response, which appears predominantly in the quadrature output, as opposed to the eddy current response, which appears predominantly in the in-phase component.

In principle, the coils could be replaced by two magnetometer sensors of other types (fluxgate, magnetoresistive, magnetoimpedance, etc.). Coils respond to the time derivative of the magnetic field, while the latter types of magnetometers respond to the field itself; the coil's output voltage is shifted by 90 degrees with respect to a magnetometer's. If the latter types of magnetometers are used instead of coils, then the susceptibility response would show up in the in-phase component and the eddy current response (at low frequency) in the quadrature component.

If the operating frequency is chosen much too high, both susceptibility and eddy-current responses appear in the in-phase component (using magnetometers) or quadrature component (using coils), but with opposite sign, making it impossible to distinguish between the two. At intermediate frequencies, the eddy current phase is intermediate between the two components, complicating the distinction. Therefore, it is important to choose the excitation frequency to be low enough, and preferably less than about 3000 Hz.

The substrate or coil form must be nonconductive, non-ferromagnetic and, with one possible exception, magnetically impermeable ($\mu=\mu_o$, where $\mu_o$ is the permeability of free space). The exception is that a magnetically permeable core inside sensor coils having a cylindrical geometry can increase the sensitivity of the system.

The use of a reference sensor helps to eliminate common mode error signals. For instance, a nearby passenger conveyer, such as a gurney, could contain magnetic components, but this spurious magnetization is not what is intended to detect, and, therefore, it is preferable to eliminate this magnetic source.

An audio alert, such as a buzzer, and/or an alarm light can be employed to signal the presence of an unwanted ferromagnetic object.

Figure 4:
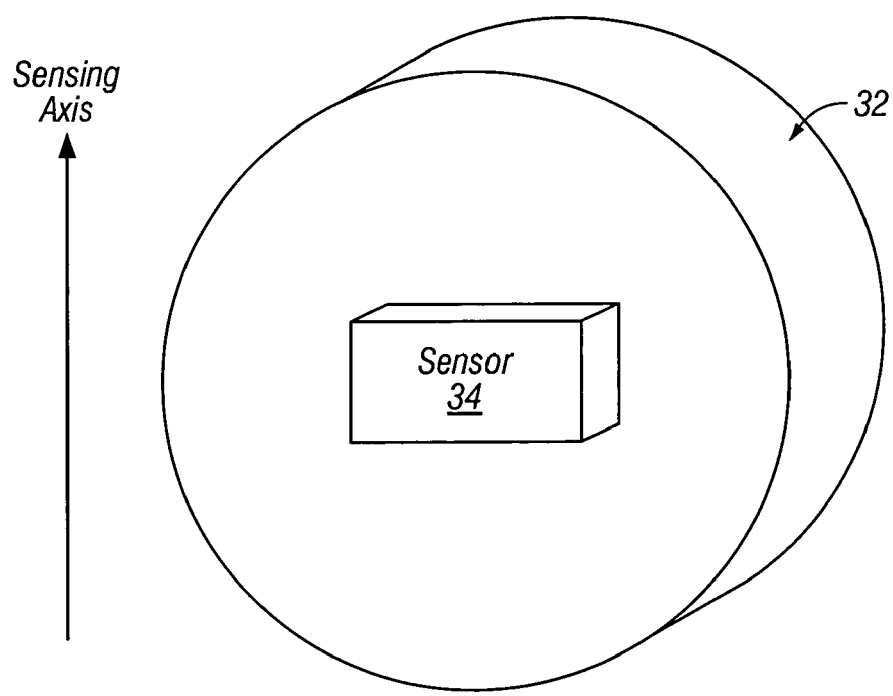
FIG. 4 is a schematic of the arrangement of a permanent magnet source relative to the sensing axis of the sensor.

As shown in FIG. 4, the sensor's sensitivity axis is orthogonal to the axis of the magnetic field of a permanent magnet 32. Otherwise stated, the magnetic field of the permanent magnet 32 is normal to the plane of the sensor 34.

Figure 5:
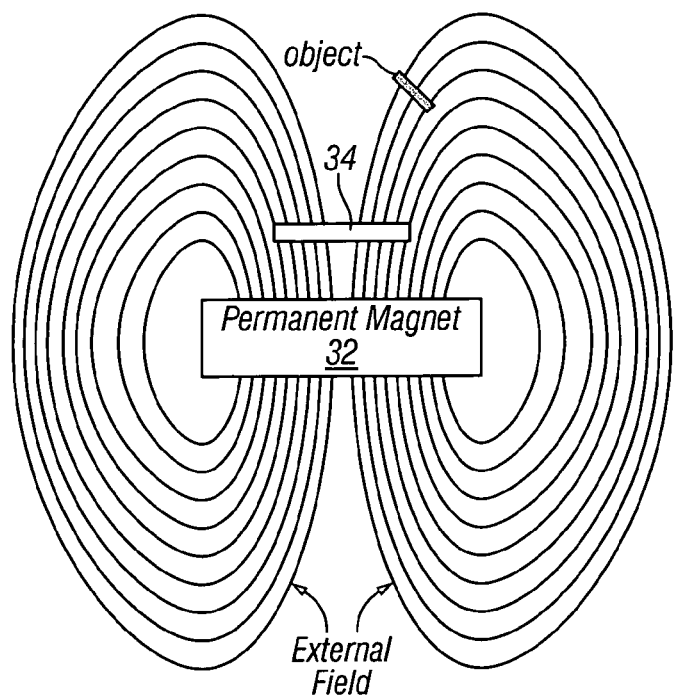
FIG. 5 is a schematic showing the arrangement of the source field from a permanent magnet, a sensor, and a ferromagnetic object.
Figure 6:
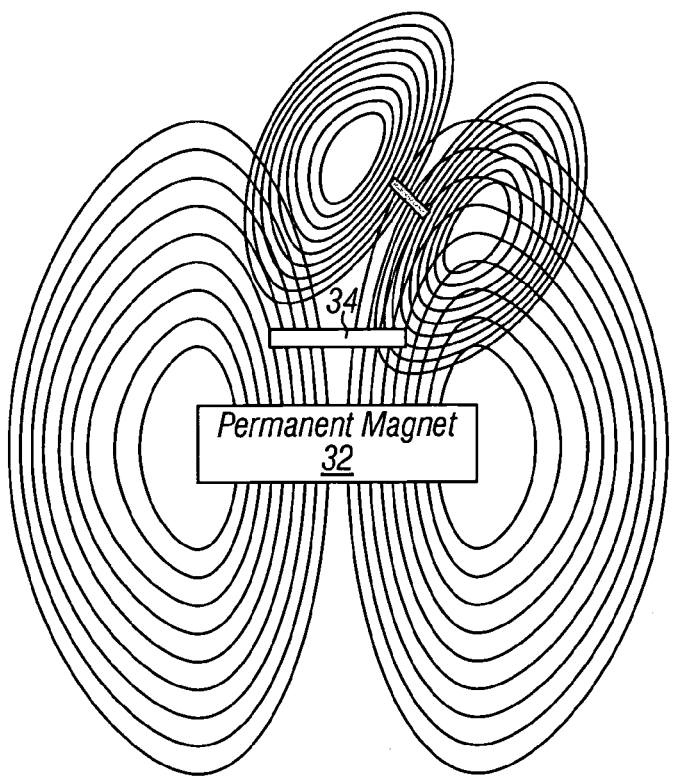
FIG. 6 is a schematic showing the magnetic field of the ferromagnetic object shown in FIG. 5.

In FIG. 5, the magnetic field of the DC permanent magnet field source 32 magnetizes the ferromagnetic object, which then has a magnetic field of its own, as shown in FIG. 6. This induced magnetization ("demag field") is detected by the sensor 34, triggering the alarm buzzer and/or light.

Figure 7:
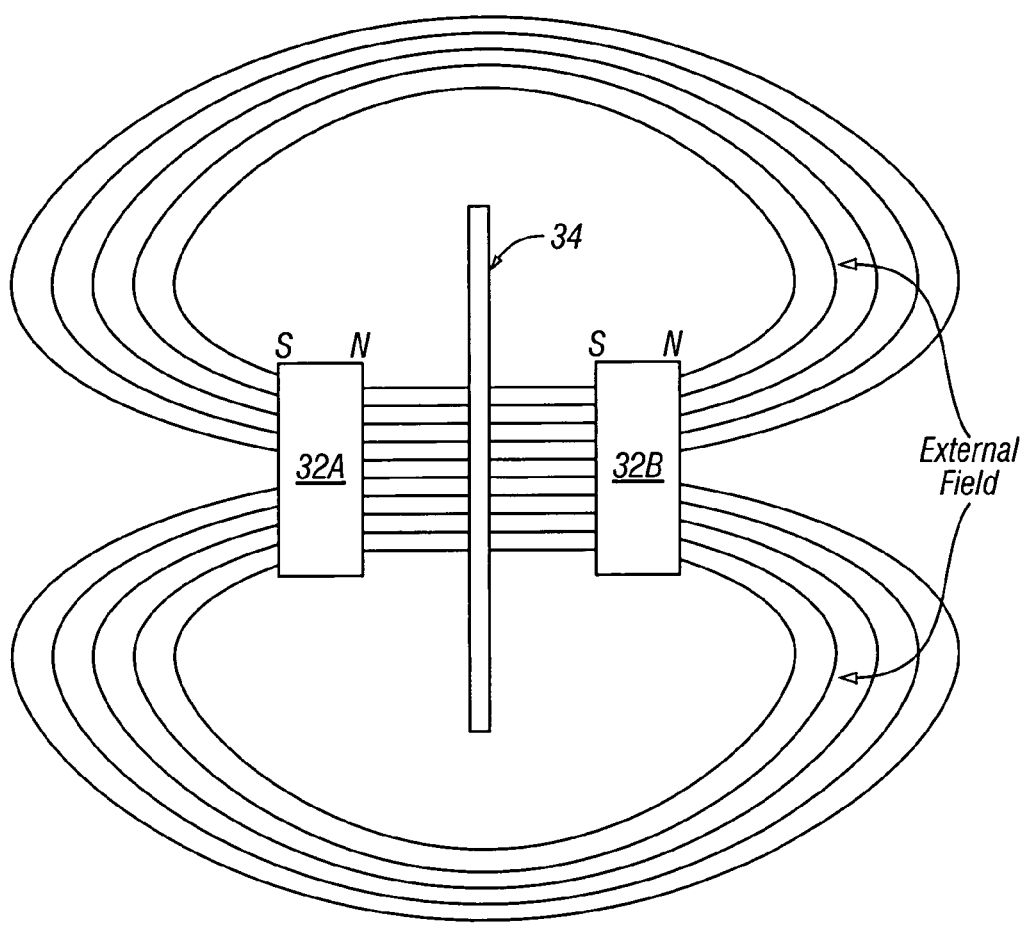
FIG. 7 is a schematic showing the arrangement of a sensor and the source field from two permanent magnets.

An alternative configuration, shown in FIG. 7, utilizes two permanent magnets 32A, 32B, as the magnetic field between them is less divergent than with a single permanent magnet. With the use of two permanent magnets 32A, 32B and less resultant divergence, there is less need for criticality about positioning the permanent magnet with respect to the sensor 34.

FIGS. 8 through 13 show various embodiments of the excitation coil configurations useful with the portal structure, for applying a magnetizing field to the volume of space around a portal. For the sake of illustration, the portal is assumed to comprise a set of single-axis magnetic field gradiometers in two substantially equal arrays on either side of the opening. The principles can be generalized to portals with gradiometers in other orientations, and with multi-axis gradiometers as well.

The underlying requirement of the applied field is that it should not disturb the sensors. That is, in the absence of a magnetic or magnetizable object in the portal, the field should produce zero signal on the gradiometer outputs. This requirement ensures that variations in the applied field don't show up as noise on the sensors—since the objective is to increase the signal from objects, by increasing the magnetizing field, without increasing the sensor noise.

The requirement can be stated as follows: the magnetizing field should have zero mutual inductance with the sensors. This can be expressed in two forms, with the same net result but with slightly different implementation issues. In one form, the magnetizing field has zero mutual inductance with each magnetometer (a pair of them making one gradiometer). This is a more restrictive requirement than the second form, which specifies zero mutual inductance with each gradiometer.

Assume a coordinate system in which the z-axis points vertically, the x-axis horizontally in the plane of the portal, and the y-axis orthogonally to the plane of the portal. FIGS. 8 through 13 all assume gradiometers measuring the difference in the x-direction of the x-component of the field (written as $\partial B_x/\partial x$). FIGS. 8 through 11 illustrate the first form of the requirement (zero coupling to each magnetometer); this is achieved by making the field point entirely in the y-direction (orthogonally to the sensitive axis) at all the sensors.

FIGS. 8 and 9 illustrate a single coil substantially in the portal plane, with FIG. 8 showing the front elevation of the portal, and FIG. 9 showing the right side elevation. This coil generates a magnetic field substantially parallel to the y axis. Not only is the illustrated coil 40 in the plane of the portal, or as close as possible to it, but the vertical legs run midway between each pair of magnetometers 42A, 42B making up the gradiometer pair 42. Thus, not only is the field perpendicular to the magnetometers' sensitive axis, but each sensor of the pair sees the same field, so any residual field gets canceled on subtraction of one sensor signal from the other, to form the gradient measurement. The coil 40 need not be higher or lower than the portal panels 43A, 43B; the components are just shown this way for clarity.

FIGS. 10 and 11 show a pair of coils 44, 46 on either side of the portal plane, with FIG. 10 showing the front elevation of the portal, and FIG. 11 showing the right side elevation. This configuration also generates a magnetic field substantially parallel to the y axis. This optimum arrangement is as a Helmholtz coil pair, but this is not mandatory. The Helmholtz configuration gives the best field uniformity over the portal aperture, but it can add some bulkiness to the apparatus, which can create a problem in some applications, such as an especially "space-challenged" MRI facility. The two coils 44, 46 overlap. Current runs in the same direction, clockwise in FIG. 10, in both coils.

FIGS. 12 and 13 illustrate the second form of the requirement (zero mutual inductance with each gradiometer). In this embodiment, each of two coils 48, 50 creates a field in the x-direction. FIG. 12 shows the front or back elevation of the portal, and FIG. 13 shows the side elevation. This configuration generates a magnetic field substantially parallel to the x axis. Positioning is chosen to make the magnetizing field the same at both magnetometers 42A, 42B in each gradiometer 42. Each magnetometer 42A, 42B is located at one end of one of the thin lines denoting the gradiometers 42. By making the excitation field substantially identical for each magnetometer 42A, 42B, the differential (gradient) measurement substantially cancels out the excitation field. The two coils 48, 50 overlap in the view shown in FIG. 13, and they carry current in the same direction, clockwise in the drawing.

According to the present invention, multiple excitation fields may be applied, both AC and DC, sensors can be provided across the top and bottom of the portal, and a door interlock can be provided to insure that the controlled area is not accessed in the absence of a negative result from the scanning process.

Figure 14:
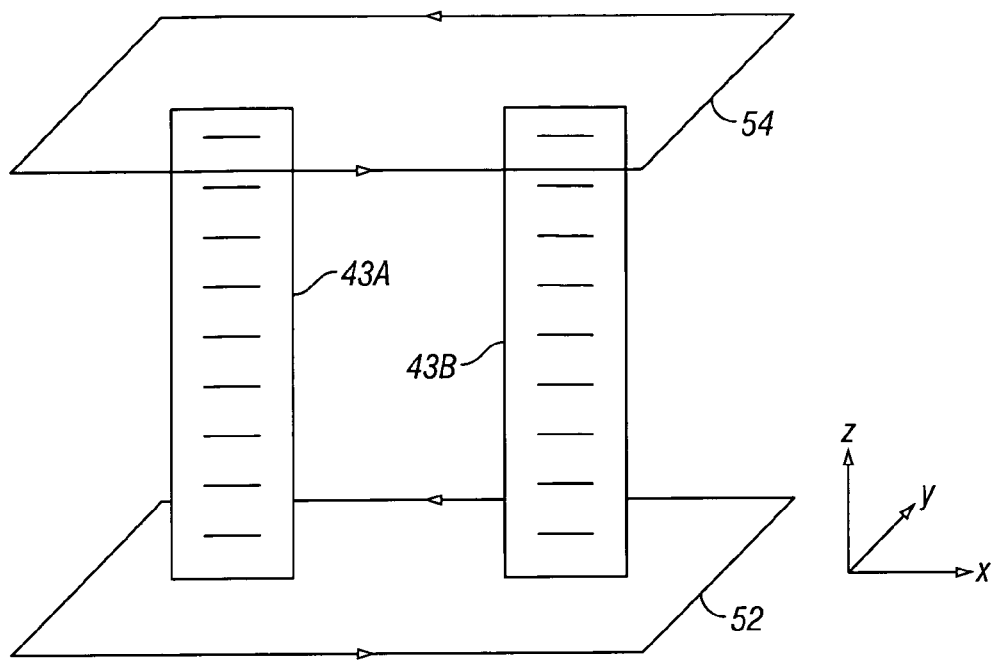
FIG. 14 shows a fourth embodiment of the excitation coil configuration relative to the portal structure.
Figure 15:
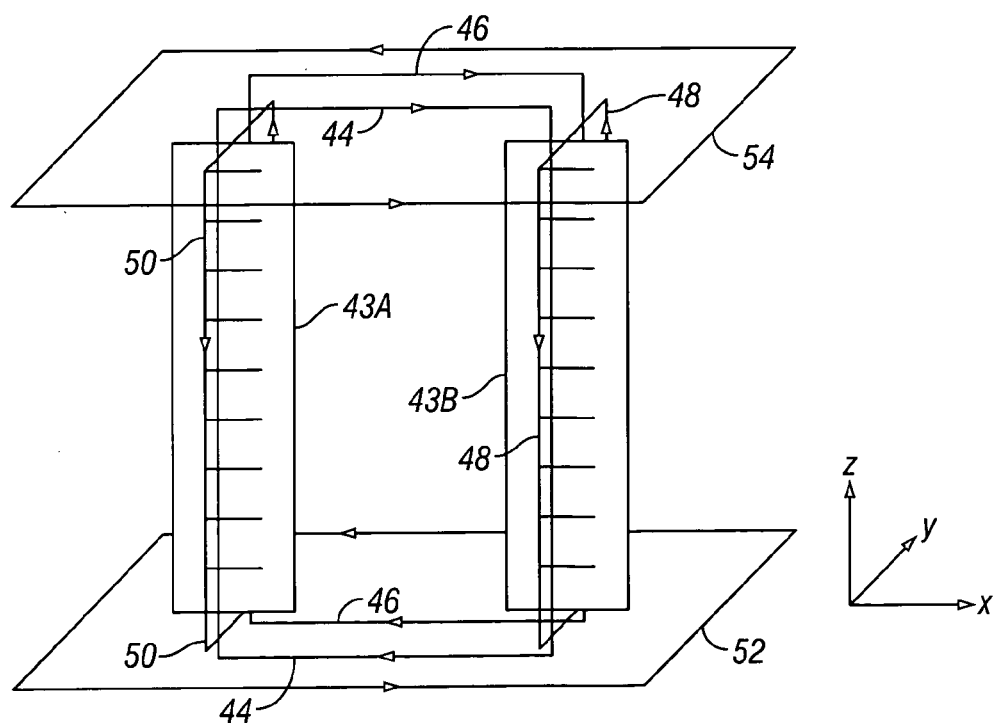
FIG. 15 shows a combination of the excitation coil configurations shown in FIGS. 8 through 14.

As shown in FIG. 14, in addition to the excitation coil configurations shown in FIGS. 8 through 13, an excitation source can be provided to generate a magnetic field having its axis parallel to the z axis, that is according to the convention followed herein, a vertical magnetic axis parallel to the plane of the portal panels 43A, 43B. Such a magnetic field can be supplied by two horizontally arranged coils 52, 54 with current flow as indicated. Further, the horizontal coils 52, 54 can be combined with the coils shown in FIGS. 8 through 13, as shown in FIG. 15, to generate a magnetic field in all three axes, x, y, and z. That is, the two coil source 48, 50 generates a magnetic field having its axis horizontal and parallel to the plane of the portal, or parallel to the x axis; the two coil source 44, 46 generates a magnetic field having its axis horizontal and orthogonal to the plane of the portal, or parallel to the y axis; and the two coil source 52, 54 generates a magnetic field having its axis vertical and parallel to the plane of the portal, or parallel to the z axis. For purposes of this disclosure, the portal structure is considered to be essentially parallel to the x-z plane, and passage of the subject to be scanned can be considered to be in the y direction.

Figure 16:
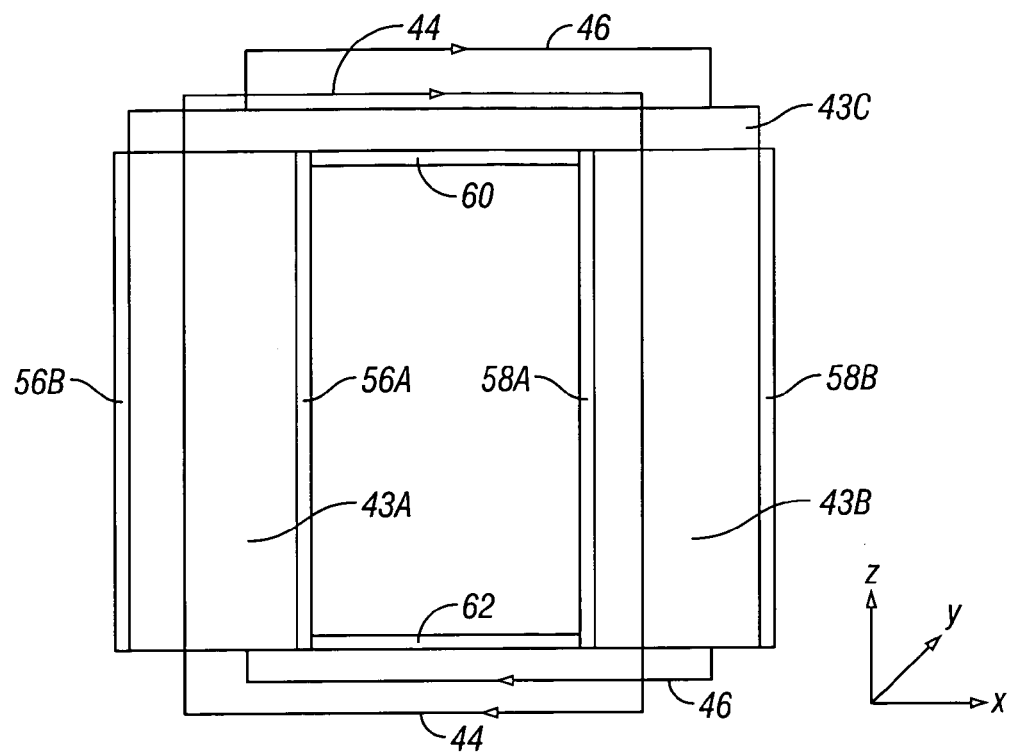
FIG. 16 shows an embodiment having permanent magnets combined with an excitation coil to generate a three axis magnetic field.

In addition to the AC and DC applied field coils, the excitation source can be a permanent magnet, such as strips of flexible ferrite magnet, or combinations of permanent magnets and applied field coils. In a preferred embodiment, as shown in FIG. 16, flexible ferrite magnet strips can be attached to the panels of the portal structure. Specifically, flexible ferrite magnet strips 56A, 56B can be attached to the inner and outer surfaces, respectively, of the left portal panel 43A, and flexible ferrite magnet strips 58A, 58B can be attached to the inner and outer surfaces, respectively, of the right portal panel 43B. These four strips generate a magnetic field having its axis horizontal and parallel to the plane of the portal, in other words, along the x axis. Further, flexible ferrite magnet strip 60 can be attached to the inner surface of the upper portal panel 43C, above the portal opening provided for passage of the subject, and flexible ferrite magnet strip 62 can be placed along the bottom of the portal opening. These two strips generate a magnetic field having its axis vertical and parallel to the plane of the portal, in other words, along the z axis. Finally, an excitation field source can be provided as two excitation coils 44, 46. These two coils generate a magnetic field having its axis horizontal and orthogonal to the plane of the portal, in other words, along the y axis.

Figure 17:
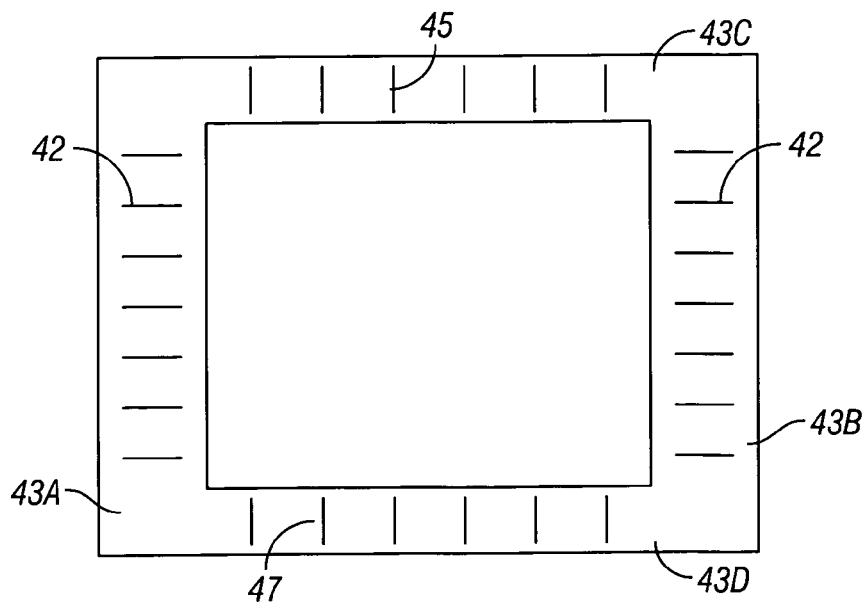
FIG. 17 shows an embodiment having sensors at the top and bottom of the portal opening, as well as on the sides.

If desired, additional sensors 45 can be provided at the top of the portal opening, and additional sensors 47 can be provided at the bottom of the portal opening, as shown in FIG. 17. The top sensors 45 can provide more sensitive scanning of the head area of the subject, while the bottom sensors 47 can provide more sensitive scanning of the foot area of the subject. It may be necessary to provide a ramp at the bottom of the portal opening for foot traffic over the bottom sensors 47.

Figure 18:
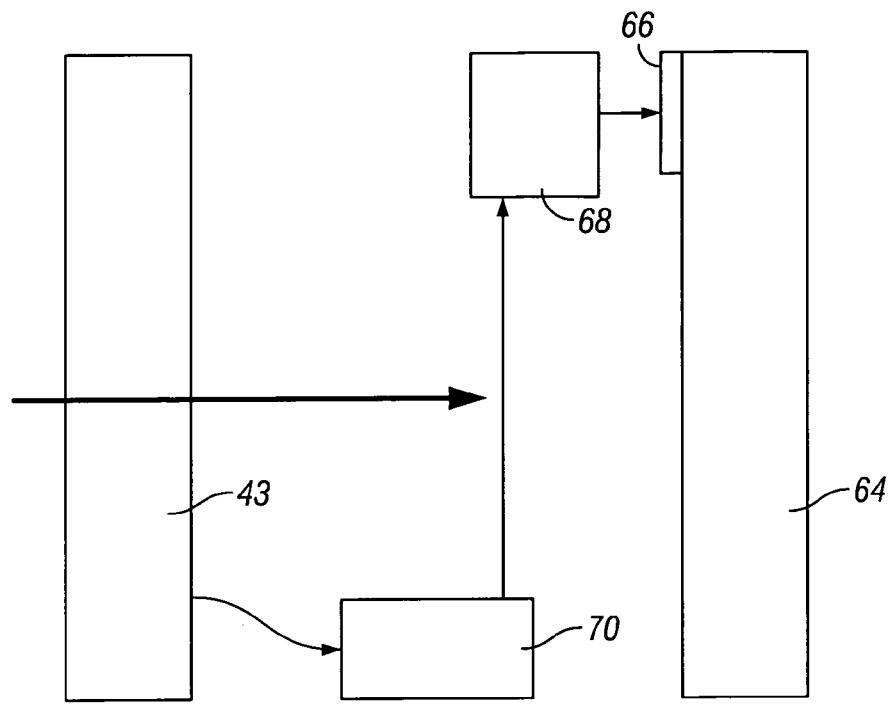
FIGS. 18 and 19 show embodiments having a door interlock.
Figure 19:
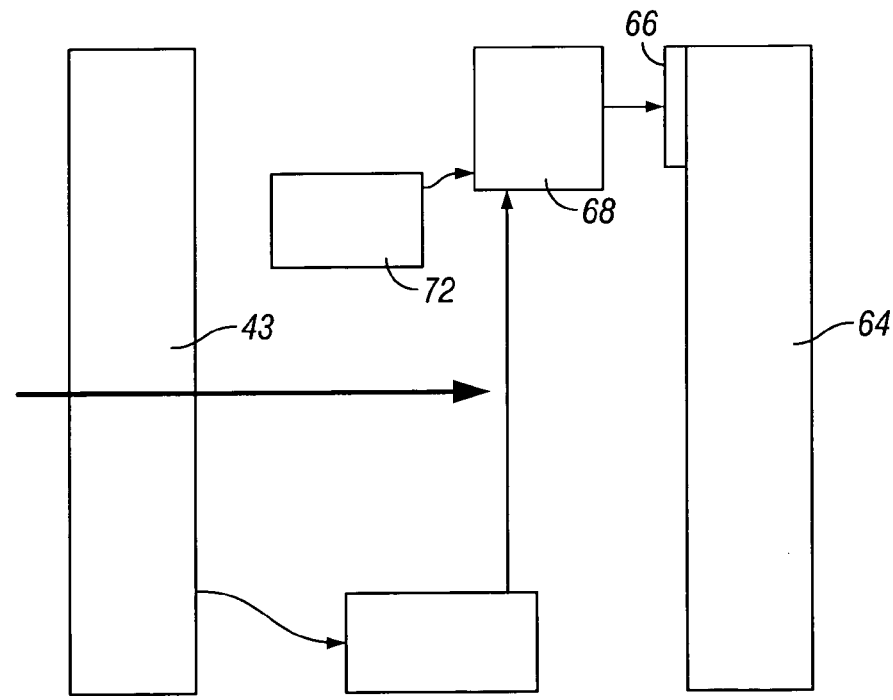

Further, as shown in FIGS. 18 and 19, a lock 66 can be provided on the door 64 to the controlled area. The processor 70 which receives and interprets the signals from the sensors on the portal 43 controls an interlock circuit 68 which enables the unlocking of the lock 66 only in the event of a successful scanning of a subject without detecting a ferromagnetic object. A keypad or magnetic card reader 72 can also be provided, with the interlock circuit 68 taking an open signal from the keypad or card reader 72, and enabling the unlocking of the lock 66.

While the particular invention as herein shown and disclosed in detail is fully capable of obtaining the objects and providing the advantages hereinbefore stated, it is to be understood that this disclosure is merely illustrative of the presently preferred embodiments of the invention and that no limitations are intended other than as described in the appended claims.

We claim:

1. An apparatus for excluding objects from introduction into a controlled area, comprising:
   a portal structure with an opening for passage of a subject to be scanned;
   an array of magnetic field sensors mounted on said portal structure adapted to sense an induced magnetic field of an object in at least one sensitive axis;
   at least one excitation source establishing at least one magnetic excitation field adapted to induce said magnetic field of said object, said at least one excitation source being oriented to cause said at least one excitation field to have a substantially zero mutual inductance with said sensors; and
   a processor adapted to interpret signals from said sensors to indicate the presence of said object;
   wherein said at least one excitation source comprises at least one permanent magnetic source.

2. The apparatus recited in claim 1, wherein:
   each said sensor comprises a single magnetometer having at least one sensitive axis; and
   said at least one excitation source is oriented to cause said at least one excitation field to have a substantially zero mutual inductance with said at least one sensitive axis of each of said magnetometers.

3. The apparatus recited in claim 2, wherein said at least one magnetometer comprises an induction coil magnetometer.

4. The apparatus recited in claim 2, wherein said at least one magnetometer comprises a magnetoresistive magnetometer.

5. The apparatus recited in claim 1, wherein each said sensor comprises a gradiometer including a pair of magnetometers, each of said magnetometers being oriented to have its said at least one sensitive axis parallel to said at least one sensitive axis of said other magnetometer of said pair.

6. The apparatus recited in claim 5, wherein said at least one excitation source is oriented to cause said at least one excitation field to have a substantially zero mutual inductance with said at least one sensitive axis of each of said magnetometers.

7. An apparatus for excluding objects from introduction into a controlled area, comprising:
   a portal structure with an opening for passage of a subject to be scanned;

an array of magnetic field sensors mounted on said portal structure adapted to sense an induced magnetic field of an object in at least one sensitive axis;

at least one excitation source establishing at least one magnetic excitation field adapted to induce said magnetic field of said object, said at least one excitation source being oriented to cause said at least one excitation field to have a substantially zero mutual inductance with said sensors; and a processor adapted to interpret signals from said sensors to indicate the presence of said object, wherein:

said at least one sensitive axis of each said sensor comprises three sensitive axes;

a first said sensitive axis is a horizontal axis lying substantially parallel to the plane of said portal structure;

a second said sensitive axis is a horizontal axis lying substantially orthogonal to the plane of said portal structure; and a third said sensitive axis is a vertical axis lying substantially parallel to the plane of said portal structure.

8. The apparatus recited in claim 1, wherein:

said sensor array comprises first and second sub-arrays of said sensors;

said first sub-array is arranged on the left side of said portal opening, relative to the path of said subject being scanned; and said second sub-array is arranged on the right side of said portal opening, relative to the path of said subject being scanned.

9. An apparatus for excluding objects from introduction into a controlled area, comprising:

a portal structure with an opening for passage of a subject to be scanned;

an array of magnetic field sensors mounted on said portal structure adapted to sense an induced magnetic field of an object in at least one sensitive axis;

at least one excitation source establishing at least one magnetic excitation field adapted to induce said magnetic field of said object, said at least one excitation source being oriented to cause said at least one excitation field to have a substantially zero mutual inductance with said sensors; and a processor adapted to interpret signals from said sensors to indicate the presence of said object, wherein:

said sensor array comprises first and second sub-arrays of said sensors;

said first sub-array is arranged on the left side of said portal opening, relative to the path of said subject being scanned;

said second sub-array is arranged on the right side of said portal opening, relative to the path of said subject being scanned; and said sensor array further comprises a third sub-array of said sensors arranged above said portal opening.

10. An apparatus for excluding objects from introduction into a controlled area, comprising:

a portal structure with an opening for passage of a subject to be scanned;

an array of magnetic field sensors mounted on said portal structure adapted to sense an induced magnetic field of an object in at least one sensitive axis;

at least one excitation source establishing at least one magnetic excitation field adapted to induce said magnetic field of said object, said at least one excitation source being oriented to cause said at least one excitation field to have a substantially zero mutual inductance with said sensors; and a processor adapted to interpret signals from said sensors to indicate the presence of said object, wherein:

said sensor array comprises first and second sub-arrays of said sensors;

said first sub-array is arranged on the left side of said portal opening, relative to the path of said subject being scanned;

said second sub-array is arranged on the right side of said portal opening, relative to the path of said subject being scanned; and said sensor array further comprises a third sub-array of said sensors arranged below said portal opening.

11. An apparatus for excluding objects from introduction into a controlled area, comprising:

a portal structure with an opening for passage of a subject to be scanned;

an array of magnetic field sensors mounted on said portal structure adapted to sense an induced magnetic field of an object in at least one sensitive axis;

at least one excitation source establishing at least one magnetic excitation field adapted to induce said magnetic field of said object, said at least one excitation source being oriented to cause said at least one excitation field to have a substantially zero mutual inductance with said sensors; and a processor adapted to interpret signals from said sensors to indicate the presence of said object, wherein:

said sensor array comprises first and second sub-arrays of said sensors;

said first sub-array is arranged on the left side of said portal opening, relative to the path of said subject being scanned;

said second sub-array is arranged on the right side of said portal opening, relative to the path of said subject being scanned; and said sensor array further comprises third and fourth sub-arrays of said sensors;

said third sub-array is arranged above said portal opening; and said fourth sub-array is arranged below said portal opening.

12. The apparatus recited in claim 1, wherein said at least one permanent magnetic source comprises a plurality of permanent magnetic sources, each said permanent magnetic source being arranged with its magnetic field orthogonal to each other magnetic field of said at least one excitation source.

13. The apparatus recited in claim 12, wherein said plurality of permanent magnetic sources comprises at least two permanent magnetic sources, each said permanent magnetic source being arranged with its magnetic field orthogonal to each other magnetic field of said at least one excitation source.

14. The apparatus recited in claim 13, wherein each said permanent magnetic source comprises at least two permanent magnets, each said permanent magnet having its magnetic field axis substantially parallel to the magnetic field axis of another said permanent magnet of said permanent magnetic source, said at least two permanent magnets of said permanent magnetic source being positioned on opposite sides of said portal opening.

15. The apparatus recited in claim 14, wherein:

said at least two permanent magnets of a first said permanent magnetic source have magnetic field axes substantially parallel to the plane of said portal structure, with at least one said permanent magnet being on the left side of said portal opening and at least one said permanent magnet being on the right side of said portal opening, relative to the path of said subject being scanned; and said at least two permanent magnets of a second said permanent magnetic source have magnetic field axes substantially parallel to the plane of said portal structure, with one said permanent magnet being on the top side of said portal opening and the other said permanent magnet being on the bottom side of said portal opening.

16. The apparatus recited in claim 12, wherein:

said at least one excitation source further comprises an excitation coil source;

said excitation coil source comprises two excitation coils, each said excitation coil having its magnetic field axis substantially parallel to the magnetic field axis of the other said excitation coil of said excitation coil source; and said two excitation coils of said excitation coil source have magnetic axes substantially orthogonal to the plane of said portal structure, with one said excitation coil being on the front side of said portal opening, and the other said excitation coil being on the back side of said portal opening, relative to the path of said subject being scanned.

17. An apparatus for excluding objects from introduction into a controlled area, comprising:

a portal structure with an opening for passage of a subject to be scanned;

an array of magnetic field sensors mounted on said portal structure adapted to sense an induced magnetic field of an object in at least one sensitive axis;

at least one excitation source establishing at least one magnetic excitation field adapted to induce said magnetic field of said object, said at least one excitation source being oriented to cause said at least one excitation field to have a substantially zero mutual inductance with said sensors; and a processor adapted to interpret signals from said sensors to indicate the presence of said object;

wherein said at least one excitation source comprises at least one excitation coil source; and said at least one excitation coil source comprises a plurality of excitation coil sources, each said excitation coil source being arranged with its magnetic field orthogonal to each other magnetic field of said plurality of excitation sources.

18. The apparatus recited in claim 17, wherein said plurality of excitation coil sources comprises three excitation coil sources, each said excitation coil source being arranged with its magnetic field orthogonal to said magnetic fields of the other two of said three excitation coil sources.

19. The apparatus recited in claim 18, wherein each said excitation coil source comprises two excitation coils, each said excitation coil having its magnetic field axis substantially parallel to the magnetic field axis of the other said excitation coil of said excitation coil source, said excitation coils of said excitation coil source being positioned on opposite sides of said portal opening.

20. The apparatus recited in claim 19, wherein:

said two excitation coils of a first said excitation coil source have magnetic axes substantially orthogonal to the plane of said portal structure, with one said excitation coil being on the front side of said portal opening, and the other said excitation coil being on the back side of said portal opening, relative to the path of said subject being scanned;

said two excitation coils of a second said excitation coil source have magnetic axes substantially parallel to the plane of said portal structure, with one said excitation coil being on the left side of said portal opening and the other said excitation coil being on the right side of said portal opening, relative to the path of said subject being scanned; and said two excitation coils of a third said excitation coil source have magnetic axes substantially parallel to the plane of said portal structure, with one said excitation coil being on the top side of said portal opening and the other said excitation coil being on the bottom side of said portal opening.

21. An apparatus for excluding objects from introduction into a controlled area, comprising:

a portal structure with an opening for passage of a subject to be scanned;

an array of magnetic field sensors mounted on said portal structure adapted to sense an induced magnetic field of an object in at least one sensitive axis;

at least one excitation source establishing at least one magnetic excitation field adapted to induce said magnetic field of said object, said at least one excitation source being oriented to cause said at least one excitation field to have a substantially zero mutual inductance with said sensors; and a processor adapted to interpret signals from said sensors to indicate the presence of said object;

further comprising:

a lock on a door to said controlled area;

an interlock circuit between said processor and said door lock, said processor being programmed to control said interlock circuit to unlock said door lock only in the event of passage of a subject through said portal opening without said sensors sensing an induced magnetic field of an object.

22. The apparatus recited in claim 21, wherein said at least one excitation source comprises at least one permanent magnetic source.

23. The apparatus recited in claim 21, wherein said at least one excitation source comprises at least one excitation coil source.

24. A method for excluding objects from introduction into a controlled area, comprising:

providing an array of magnetic field sensors mounted on a portal structure;

providing at least one excitation source;

providing a lock on a door to said controlled area;

establishing at least one magnetic excitation field with said at least one excitation source, while orienting said excitation source to cause said at least one excitation field to have zero mutual inductance with said sensor array;

scanning a subject with said sensor array;

inducing a magnetic field in an object, with said at least one excitation field;

sensing said induced magnetic field of said object, with said sensor array;

interpreting signals from said sensor array, with a processor, to indicate the presence of said oject; and actuating an interlock circuit between said processor and said door lock, to unlock said door lock only in the event of passage of a subject through said portal opening without said sensors sensing an induced magnetic field of an object.

25. The method recited in claim 24, wherein said at least one excitation source comprises an excitation coil, and further comprising energizing said excitation coil with alternating current.

26. The method recited in claim 24, wherein said at least one excitation source comprises an excitation coil, and further comprising energizing said excitation coil with direct current.

27. The apparatus recited in claim 21, wherein:
each said sensor comprises a single magnetometer having at least one sensitive axis; and
said at least one excitation source is oriented to cause said at least one excitation field to have a substantially zero mutual inductance with said at least one sensitive axis of each of said magnetometers.

28. The apparatus recited in claim 27, wherein said at least one magnetometer comprises an induction coil magnetometer.

29. The apparatus recited in claim 27, wherein said at least one magnetometer comprises a magnetoresistive magnetometer.

30. The apparatus recited in claim 21, wherein each said sensor comprises a gradiometer including a pair of magnetometers, each of said magnetometers being oriented to have its said at least one sensitive axis parallel to said at least one sensitive axis of said other magnetometer of said pair.

31. The apparatus recited in claim 30, wherein said at least one excitation source is oriented to cause said at least one excitation field to have a substantially zero mutual inductance with said at least one sensitive axis of each of said magnetometers.

32. The apparatus recited in claim 21, wherein:
said sensor array comprises first and second sub-arrays of said sensors;
said first sub-array is arranged on the left side of said portal opening, relative to the path of said subject being scanned; and
said second sub-array is arranged on the right side of said portal opening, relative to the path of said subject being scanned.

33. A method for excluding objects from introduction into a controlled area, comprising:
providing an array of magnetic field sensors mounted on a portal structure;
providing at least one permanent magnet as an excitation source;
establishing at least one magnetic excitation field with said at least one permanent magnet, while orienting said permanent magnet to cause said at least one excitation field to have zero mutual inductance with said sensor array;
scanning a subject with said sensor array;
inducing a magnetic field in an object, with said at least one excitation field;
sensing said induced magnetic field of said object, with said sensor array; and
interpreting signals from said sensor array, with a processor, to indicate the presence of said object.

* * * * *

UNITED STATES PATENT AND TRADEMARK OFFICE
CERTIFICATE OF CORRECTION

PATENT NO. : 7,154,266 B2 Page 1 of 1
APPLICATION NO. : 10/757029
DATED : December 26, 2006
INVENTOR(S) : Peter V. Czipott et al.

It is certified that error appears in the above-identified patent and that said Letters Patent is hereby corrected as shown below:

On the title page item (73) should read:
The assignees are MedNovus, Inc., of Leucadia, California, and Quantum Magnetics, Inc., of San Diego, California Signed and Sealed this Fourteenth Day of August, 2007

JON W. DUDAS
*Director of the United States Patent and Trademark Office*